United States Patent
Heraud

(12) 
(10) Patent No.: US 6,221,031 B1
(45) Date of Patent: Apr. 24, 2001

(54) METHOD AND IMPROVED DEVICE FOR MEASURING AND LOCATING A TOOTH APEX

(76) Inventor: Roger Heraud, 15 rue de la Garenne, F-33480 Castelnau de Medco (FR)

(*) Notice: Subject to any disclaimer, the term of this patent is extended or adjusted under 35 U.S.C. 154(b) by 0 days.

(21) Appl. No.: 09/367,955
(22) PCT Filed: Feb. 25, 1998
(86) PCT No.: PCT/FR90/00371
§ 371 Date: Aug. 24, 1999
§ 102(e) Date: Aug. 24, 1999
(87) PCT Pub. No.: WO98/37829
PCT Pub. Date: Sep. 3, 1998

(30) Foreign Application Priority Data

Feb. 25, 1997 (FR) .................................................. 97 02572

(51) Int. Cl.⁷ ...................................................... A61B 5/00
(52) U.S. Cl. .......................................... 600/590; 600/547
(58) Field of Search .................................... 600/547, 587, 600/589, 590

(56) References Cited

U.S. PATENT DOCUMENTS

| | | | |
|---|---|---|---|
| 3,993,044 | * 11/1976 | McGiffin | 128/776 |
| 4,447,206 | * 5/1984 | Ushiyama | 600/589 |
| 4,526,179 | * 7/1985 | Sadesky | 128/776 |
| 5,096,419 | * 3/1992 | Kobayashi et al. | 600/589 |
| 5,112,224 | * 5/1992 | Shirota | 600/589 |

FOREIGN PATENT DOCUMENTS

3018568 * 11/1980 (DE).
95/13032 * 5/1995 (WO).

* cited by examiner

*Primary Examiner*—Max Hindenburg
(74) *Attorney, Agent, or Firm*—Young & Thompson

(57) ABSTRACT

A process and a device for measuring and locating the apex of a root canal of a tooth, by measuring, between a rasp forming an electrode inserted in the root canal and a second electrode disposed in the mouth, the variations of time constants of resistances and capacitances encountered in the canal, includes applying to the terminals of the electrodes a continuous current signal or a square signal of current of predetermined frequency for repeating the measurements and carrying out at the terminals of the electrodes at least two measurements for a given alternation so that a radiometric computation of the measurements can be obtained which result represents a distance separating the distal end of the rasp from the apex.

16 Claims, 3 Drawing Sheets

METHOD AND IMPROVED DEVICE FOR MEASURING AND LOCATING A TOOTH APEX

BACKGROUND OF THE INVENTION

The present invention relates to an improved process and device for locating the apex of a tooth.

More exactly, the invention provides a process and device for measuring in real time the distance between the distal end of an electrode inserted in the root canal of a tooth and the apex of said canal, this measurement being insensitive to anything other than the pulp, in said canal, of blood, pus, debris, water or antiseptics such as hydrogen peroxide, sodium chloride or sodium hypochlorite.

DESCRIPTION OF THE RELATED ART

The location of the apex or the apical constriction is important in the procedure of treating the dental canal because the success of the latter depends on the total removal of the pulp tissue.

To this end, the dentist uses a metallic endocanal rasp which slides in the root and, by its movement of rotation and back-and-forth movement, it scrapes the walls of the canal so as to depulp it and to descend more and more deeply into the root, and this without extending beyond the apical constriction, which can cause trouble for the patient and lead to an abscess.

It is therefore important to be able to locate precisely the apex of the root to be cleaned.

For this purpose, several processes have been used.

The process most used at present consists in inserting a rasp into the canal by successive approaches and monitoring with a succession of x-ray samples to place the rasp in position at the apex.

Then the dentist adjusts the abutment of the rasp against a cuspid scale to determine the depth of the canal.

This technique is inadequate and undesirable because of the dose of radiation to which the patient is subjected or because of curves in the canal or a lateral apex, which is a source of errors of reading and of analysis of the samples.

Another process (U.S. Pat. No. 5,049,069) based on the discovery that the measurement of electrical impedance between an electrode placed at the apex and a reference electrode placed in the mouth of the patient, gives a constant value no matter what the apex and no matter what the patient. It has been established that between the apex and a point along the root canal, the impedance was proportional to the distance between said point and the apex over several millimeters.

These processes, based on this discovery, are not reliable, because the measurement depends on variations of impedance at the level of the reference electrode disposed in the mouth of the patient.

They are adjusted for a measurement made in a sound pulp and they do not function in media such as hypochlorite, sodium chloride, blood, etc. because the impedance of the medium is modified.

Another more reliable process (French patent 93/13802) operates with canal media, known in advance, using measurements of impedance between an electrode such as a rasp inserted in the dental canal and two other reference electrodes connected to the lip of the patient, and permits eliminating errors due to variations of the reference contacts and hence to increase the reliability of the measurement. It can measure in blood or in very conductive media such as hypochloride, by creating a staged offset of origin of the resistivity of the medium.

Another process (U.S. Pat. Nos. 5,080,586 and 5,112,224) uses two impedance measurements at two different frequencies, for example 1 khz and 5 khz, between an electrode such as a rasp inserted in the root canal and an electrode abutting the oral mucosa, the impedances not having the same frequency response upon approaching the apex. There is carried out a substraction of the two measurements. This difference in approaching the apex will give the measurement. This process provides a manual or automatic zero reset of the output of the subtractor, by a button or a detection, when the rasp has been inserted in the canal, acting on a memorized offset of one of the inputs of the subtractor, and permits determining the movement of a zero reset at the output. A difference between the impedances having frequent respective frequency responses discloses at a specified value the position of the apical opening (FR 2.668.701-A1).

This process requires a calibration for each canal to be measured, which is hardly practical or is a source of errors in current usage.

Another process (U.S. Pat. No. 5,096,419) uses two impedance measurements at two different frequencies, for example 400 hz and 8 khz, between an electrode such as a rasp inserted in the root canal and an electrode abutting on the oral mucosa, the impedances having not the same response in frequency to the approach of the apex. There is carried out a ratio of the two measurements to eliminate the variation of the impedances due to the media in which the rasp is located in the canal.

This process gives errors when the medium becomes insulating such as hydrogen peroxide. Thus the responses of the two frequencies are no longer entirely ratiometric.

SUMMARY OF THE INVENTION

The present invention provides a different measurement process, without calibration, independent of the medium in the canal, and of high precision.

The present invention provides a process for locating the apex of a root canal of a tooth and/or for measuring the canal distance by means of the measurement of variations of time constants of the resistances/capacitances encountered, between an electrode such as a dental rasp inserted in the root canal, and a second electrode disposed for example on the buccal mucosa of the patient, characterized in that:

There is applied to the terminals of the electrodes a current or a given continuous voltage.

A square signal of predetermined frequency permits repetition of the measurements in real time, creating positive and negative alternation.

After amplification, the origin of the measurements is fixed at the level obtained at 0 $\mu$S.

There are thus carried out two time measurements of the alternation.

It will be noted on FIGS. 5 and 6, that one measurement (A) develops very little when the rasp is located between 5 mm and 1.5 mm, and revolves more in the region of the apex, whilst measurement (B) develops in a substantially linear manner.

A ratiometric computation of the measurements (A) and (B) is then carried out to eliminate the effect of perturbances such as the change of medium, the change of diameter of the rasps;

$$M = \frac{A}{B} - K1 \text{ or } M = K1 - \frac{B}{A}$$

The squared measurements before computation of the ratio give a better linearity, thus the development of the signal to be measured is exponential.

The formulae operate for conductive media and very conductive media, they operate a bit less well in media that are hardly conductive, such as hydrogen peroxide.

To be less sensitive to the less conductive media:

There is carried out in time three measurements alternately. A measure (A) and a measure (B) carried out as before and a measure (C) as shown in FIGS. 5 and 6 which develops in the portion between 5 mm and 0.5 mm and very little in the region of the apex.

There is carried out the computation $$M = \frac{A * C}{B * B} - K1$$

or the calculation $$M = K1 - \frac{B * B}{A * C}$$

So as to attain a final result of the distance on the desired scale, the value M is multiplied by a suitable coefficient, which represents the distance comprised between the distal end of the rasp and the apex.

For the preceding radiometric computation, K1 is a known constant and permits obtaining location of the apex at a value located at zero voltage for example.

If a measurement is made with negative alternation, there is applied a current or a voltage of opposite direction. The resulting M will be inverted.

The measurements will be measurements of voltage at the terminals of the electrodes if the signal applied to the electrodes is a current.

The measurements will be measurements of current passing through the electrodes if the signal applied to the electrodes is a voltage.

The measurements are carried out with positive and/or negative alternation.

The present invention also provides a device for practicing the process of the invention, comprising an electrode inserted in the root canal and a second electrode disposed in the mouth, characterized in that it comprises moreover:

Means to apply a square signal to the terminals of the electrodes;

Measuring means to obtain at least two values of voltage for a given alternance;

Means for computing and processing the measured values, to determine the distance between the distal end of the electrode inserted in the canal and the apex of said canal;

Display means to display said distance thus determined.

Preferably, the means to apply a square signal are constituted by a current generator and the measurements carried out are measurements of voltage at the terminals of the electrodes.

It should be noted that the graph described above simply gives qualitative information as to the observed signals, and no quantitative information whatsoever can be determined therefrom.

DESCRIPTION OF THE PREFERRED EMBODIMENTS

Figure 1:
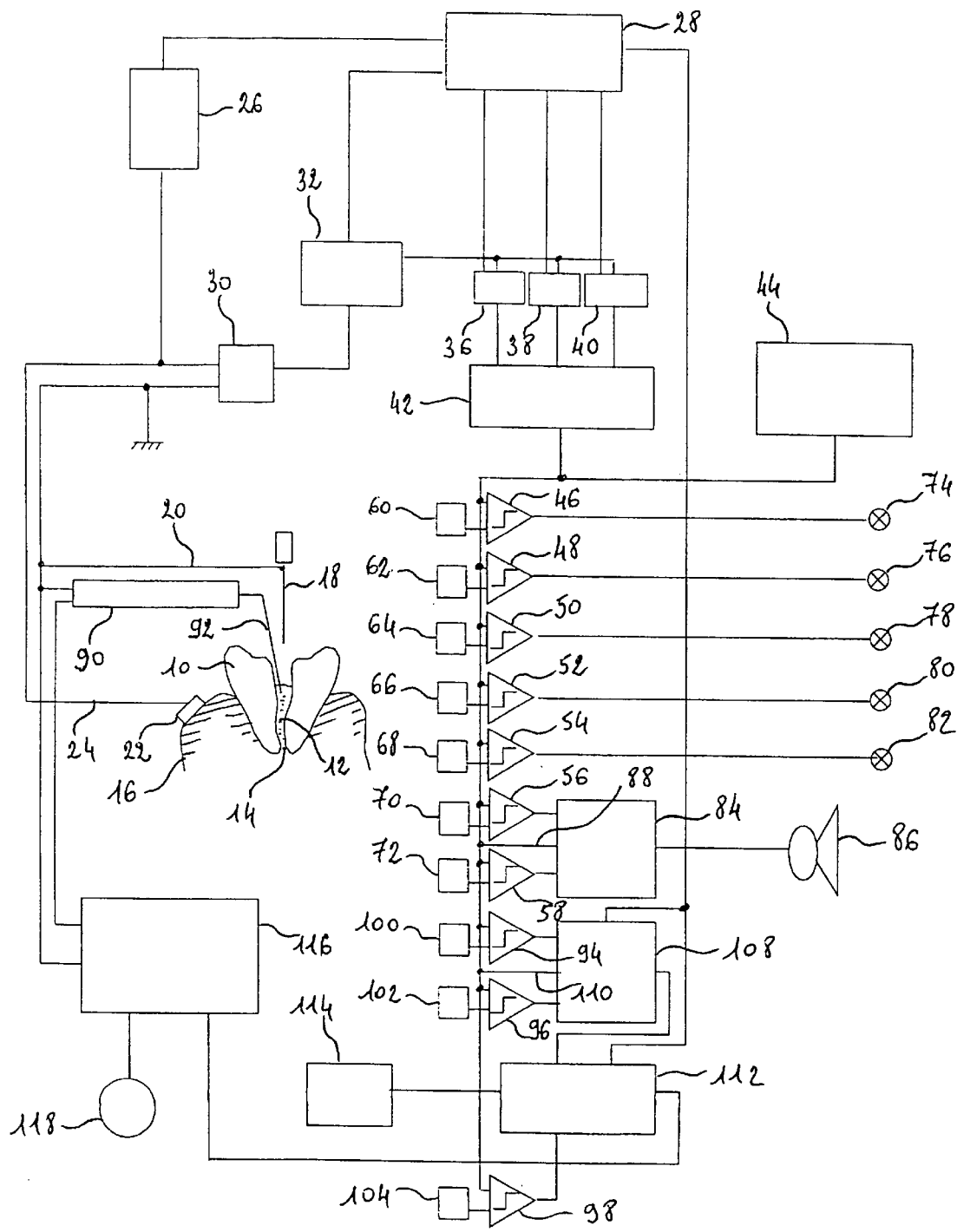
FIG. 1 is a diagram of an embodiment of a device for practicing the process of the invention.

In FIG. 1 there is shown in cross-section a tooth 10 comprising a root canal 12 terminating in an apex 14, the gums and the buccal tissues being shown at 16.

An endodontic rasp 18, located in the canal 12, is an electrode connected to a flexible conductive wire 20 which is connected to the ground. A second electrode 22, connected to a flexible conductive wire 24, is opposed against the buccal mucosa 16 of the patient.

The wire 24 is connected to a module 26 itself connected to a sequencer 28 which generates a square signal of predetermined frequency and amplitude.

The module 26 comprises a circuit adapted to limit the substantially constant current intensity flowing through the tooth of the patient and to suppress the continuous component at the terminals of the electrodes 18, 22. There can for example be a high ohmic resistance R in series with the condenser C of suitable capacitance.

The voltage at the terminals of the electrodes 18, 22 is amplified and measured by an amplifier 30 whose output is connected to an analog-digital converter 32 synchronized by the sequencer 28.

The converter 32 is connected to three memories 36, 38, 40, respectively synchronized by the sequencer 28.

The memories 36, 38, 40 are connected to a computation unit 42.

The output of the unit 42 is connected to a digital and/or analog display 44 and has comparators 46, 48, 50, 52, 54, 56, 58, respectively connected to comparison memories 60, 62, 64, 66, 68, 70, 72.

The comparators 46, 48, 50, 52, 54 are connected to luminous signals 74, 76, 78, 80, 82, whilst the comparators 56, 58 are connected to a modulator 84 connected to a sonic warning 86. The modulator 84 is also connected to the output of the module 42, by a wire 88.

The computation unit 42 is also connected to comparators 94, 96, 98, respectively connected to memories 100, 102, 104. The comparator 94, 96 are connected to a modulator 108 synchronized by the sequencer 28. Like the modulator 84, the modulator 108 is connected to the output of the computation unit 42 by a wire 110. The output of the modulator 108 is connected to a mode switch 112 synchronized by the sequencer 28.

The mode switch is connected to a mode selector 114 and to the comparator 98. The output of the mode switch 112 is connected to a rotational speed regulator 116 comprising means to adjust the speed 118, said regulator 116 piloting a rotatable electric motor 90 associated with a counter angle supporting a continuously rotating rasp 92.

The block 116 can also be an ultrasonic oscillator comprising power adjustment means 118, said oscillator 116 controlling the oscillations of the rasp 92.

The process of the present invention is described in detail below with respect to the device described above, which represents a preferred but non-limiting embodiment.

Figure 2:
FIG. 2 is a graph showing qualitatively the square voltage applied by the sequencer.

The sequence 28 generates a square signal of 50 hz such as that of FIG. 2.

Figure 3:
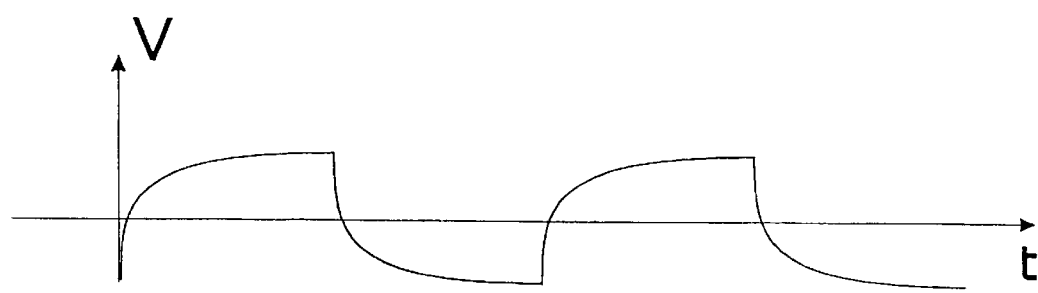
FIG. 3 is a graph illustrating qualitatively the voltage at the terminals of the two electrodes.

The voltage at the terminals of the electrodes 18, 22 is as in FIG. 3.

The signal obtained at the terminals of the electrodes 18, 22 is a function of the variations of the time constants of the resistances/capacitances encountered in the canal, the latter has an amplitude which is connected to the medium in which the electrode 18 is located. Between the conductive medium and a non-conductive medium, it is noted that the amplitude is less in a conductive medium.

The measurement is zeroed in front of the signal period at 0 $\mu S$ which is the beginning of alternation.

Figure 4:
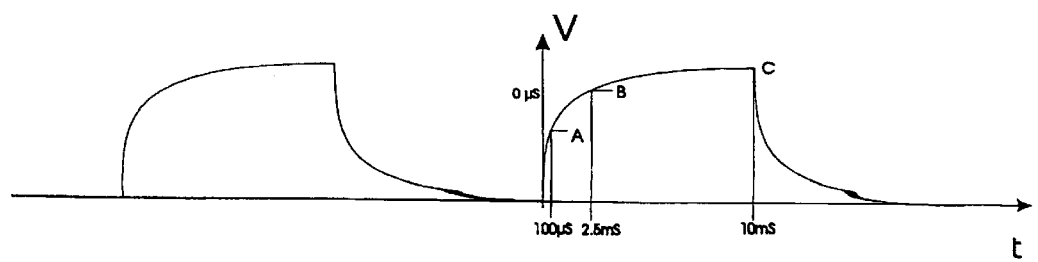
FIG. 4 is a graph illustrating qualitatively, for positive alternants, the different measurements effected.

As shown in FIG. 4, which represents a positive alternation of the voltage at the terminals of the electrodes 18, 22, there are carried out three voltage measurements A, B, C, respectively at 100 $\mu S$, 2.5 mS, 10 mS at the beginning of alternation. These measurements are stored in memories 36, 38, 40.

Figure 5:
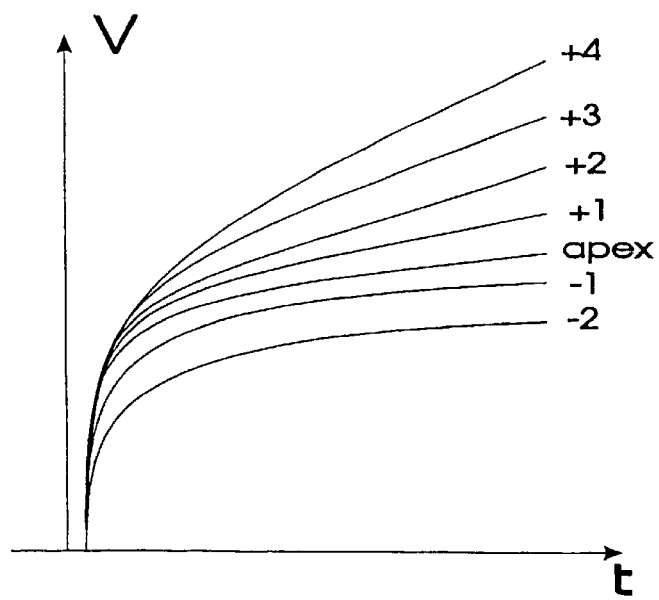
FIG. 5 is a graph illustrating qualitatively the variations noted for different distances separating the measurement electrode from the apex.
Figure 6:
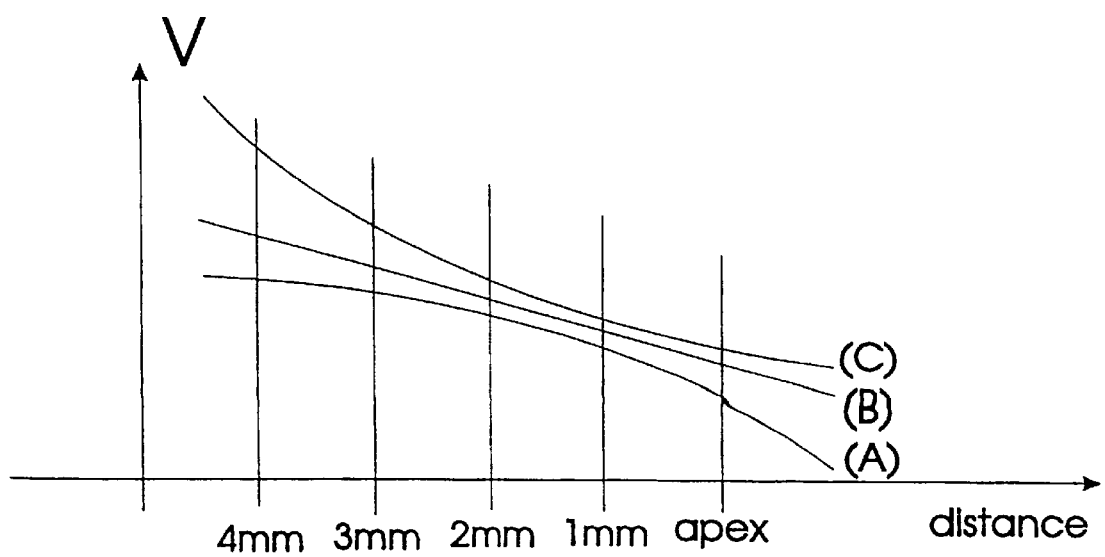
FIG. 6 is a graph showing qualitatively the variation of two measurement points as a function of the distance to the apex.

It can be seen in FIGS. 5 and 6 that the measurement A develops very much less in the portion in which the rasp is located between 5 mm and 1.5 mm, and develops in the region of the apex, whilst a measurement C develops in the portion between 5 mm and 0.5 mm and very little in the region of the apex. A measurement B located at 2.5 mS evolves substantially linearly.

The computation unit 42 carries out the following computation:

$$M = \frac{A * C}{B * B} - K1$$

K1 is a constant obtained experimentally

K1 is a constant equal to $(A*C)/(B*B)$ when the distal end of the rasp is at the apex of a tooth, which gives 0 for M.

The assembly remains ratiometric no matter what the medium encountered in the canal and of the diameter of the rasp.

The linearity is sufficient over the range of measurement.

So as to obtain a final result of the distance on the desired scale, the value M is multiplied by a suitable coefficient, which represents the distance comprised between the distal end of the rasp 18 and the apex 14.

This final result is displayed on the module 44. The comparators 46, 48, 50, 52, 54, after having compared this final result with reference values in respective memories 60, 62, 64, 66, 68, actuates as the case may be the respective luminous signals 74, 76, 78, 80, 82.

The comparators 56, 58 compare the final result with reference values in respective memories 70, 72, and actuate as the case may be the modulator 84 so as to generate a suitable sonic signal. This permits monitoring in a visual and/or sonic manner the progressive approach of the rasp 18 to the apex 14.

The mode selector 14 permits the dentist to select between different modes of operation of the ultrasonic rasp 92.

For example, an automatic operation mode permits applying vibrations to the rasp as soon as it enters into contact with the moist medium of the canal, by comparison with memory 104.

By a suitable choice of values stored in memory 100, 102, the modulator 108 can also modify the cyclic ratio of the power applied by proceeding to short and instantaneous stoppages of the vibrations of the rasp 92.

For example, the vibration pattern of the rasp is constant when this latter is more than 2 mm from the apex, corresponding to memory 100, then, from 2 mm to 1 mm, corresponding to memory 102, the regime is modified by modification of the cyclic ratio, the vibrations decreasing progressively until stopping when the rasp is 1 mm from the apex.

Another operating mode actuates the vibrations in forced operation before insertion of the rasp into the canal, which permits treating a calcified canal which otherwise would not permit operation in an automatic mode.

Another mode actuates the vibrations solely between 2 mm and 1 mm from the apex to avoid false canals.

So as to limit errors of measurement due particularly to cavitation of the liquid about the rasp, the oscillator 116 can provide for short and momentary stops of the vibrations applied to the rasp 92, in a manner synchronized with the measurements that are carried out.

The handpiece 90 could be replaced by an endodontic counter angle, the block 116 then becoming a rotation speed regulator with a standard speed of rotation 118, the comparators 96, 98 and reference values in the associated memories 104, 102 giving rise to operation, stopping or reversal of direction of the motor of the counter angle driving a rasp in continuous rotation serving as an electrode inserted in the root canal of the tooth.

The mode selector 114 permits the dentist to select between different modes of operation of the rasp rotated by the motor and its counter angle.

For example, an automatic operational mode permits applying rotation to the rasp as soon as it enters into contact with the moist medium of the canal, by comparison with the memory 104 and to stop it by comparison with the memory 102.

Another mode of operation actuates the rotation in forced operation before insertion of the rasp into the canal, which permits treating a calcified canal which cannot be treated by automatic operation.

Of course, the present invention is not limited to the embodiments described and illustrated, but covers on the contrary all modifications, particularly as to the elements relating to use of the measurements carried out.

For example, the number of comparators and the reference values in the associated memories can be modified as a function of the desired ends.

The measurements are carried out with positive alternation, but also could be carried out with negative alternation.

What is claimed is:

1. A process for locating and measuring an apex of a tooth root canal by measuring variations of time constants of resistances and capacitances encountered between a measuring electrode forming the first electrode inserted in the root canal and a second electrode disposed in contact with mouth tissues, comprising the steps of:

applying to the first and second electrodes a square wave signal of a predetermined frequency;

establishing a measurement baseline at a level obtained at a beginning of an alternation of the square wave signal;

making two electrical measurements, A and B, in time during the alternation, computing a result M of a ratio of the two measurements with a known constant K1; and converting the result M by a coefficient to a value representing the distance separating a distal end of the first electrode from the apex.

2. Process according to claim 1, wherein the result M is given by the formula:

$$M = \frac{A}{B} - K1 \text{ or } M = K1 - \frac{B}{A}.$$

3. Process according to claim 1, wherein the result M is given by the formula:

$$M = \frac{A*A}{B*B} - K1 \text{ or } M = K1 - \frac{B*B}{A*A}.$$

4. Process according to claim 1, further comprising the steps of:

making a third measurement C during the alternation, wherein the measurement A is taken near the beginning of the alternation, the measurement C is taken remote from the beginning of alternation, and the measurement B is taken intermediate measurements A and C; and carrying out a ratiometric computation $$M = \frac{A*C}{B*B} - K1 \text{ or } M = K1 - \frac{B*B}{A*C};$$

in which K1 is a known constant.

5. Process according to claim 1, wherein the two measurements are measurements of a voltage at terminals of the first and second electrodes.

6. Process according to claim 1, wherein the two measurements are measurements of current passing through the first and second electrodes.

7. Process according to claim 1, wherein the two measurements are taken over a positive portion of the alternation.

8. Process according to claim 1, wherein the two measurements are taken over a negative portion of the alternation.

9. Process according to claim 1, wherein the two measurements are taken over a portion of a positive or a negative alternation.

10. Process according to claim 1, wherein the square wave signal applied has a frequency substantially equal to 50 hz, and the measurements A, B, and C respectively are carried out at substantially 100 $\mu$S, 2.5 mS, and 10 mS from the beginning of the alternation.

11. Device for locating and measuring an apex of a tooth root canal by measuring variations of time constants of resistances and capacitances encountered between a measuring electrode forming the first electrode inserted in the root canal and a second electrode disposed in contact with mouth tissues, comprising:

a first electrode adapted for insertion in the root canal;

a second electrode adapted for disposed in a patient's mouth;

a square wave signal source operatively connected to terminals of the first and second electrodes;

a measuring means for obtaining at least two values of voltage, A and B, over one alternation of the square wave signal;

a computational module connected to the measuring means and determining the distance between the distal end of the first electrode when inserted in the canal and the apex of the canal by computing a result M of a ratio of the two measurements A and B with a known constant K1 and converting the result M by a coefficient to a value representing the distance separating a distal end of the first electrode from the apex; and a display operatively connected to said computational module and displaying the determined distance.

12. Device according to claim 11, wherein the square wave signal source comprises a constant current generator and the measuring means is connected so that the measurements of the voltage are carried out at terminals of the first and second electrodes.

13. Device according to claim 11, wherein the display comprises a digital or an analog display.

14. Device according to claim 11, wherein the display comprises at least one comparator delivering a luminous or sonic signal when a reference value is reached.

15. Device according to claim 11, further comprising:

an ultrasonic rasp having a variable power and cyclic vibration ratio serving as another measuring electrode for insertion in the root canal of the tooth; and plural memory locations for storage of reference values, the reference values serving as a comparison basis to associated measured distances.

16. Device according to claim 11, further comprising an electric motor driving in rotation a rasp serving as another measuring electrode for insertion in the root canal of the tooth, plural memory locations for storage of reference values, the reference values serving as a comparison basis to associated measured distances.

* * * * *